United States Patent
Adrian et al.

(10) Patent No.: US 7,432,411 B2
(45) Date of Patent: Oct. 7, 2008

(54) CONTINUOUS METHOD FOR OBTAINING BUTENES FROM A C₄ FRACTION

(75) Inventors: Till Adrian, Bobenheim-Roxheim (DE); Bernd Heida, Ellerstadt (DE); Klaus Kindler, Harthausen (DE)

(73) Assignee: BASF Aktiengesellschaft, Ludwigshafen (DE)

(*) Notice: Subject to any disclaimer, the term of this patent is extended or adjusted under 35 U.S.C. 154(b) by 874 days.

(21) Appl. No.: 10/509,175

(22) PCT Filed: Apr. 29, 2003

(86) PCT No.: PCT/EP03/04435

§ 371 (c)(1),
(2), (4) Date: Sep. 27, 2004

(87) PCT Pub. No.: WO03/093202

PCT Pub. Date: Nov. 13, 2003

(65) Prior Publication Data

US 2005/0154246 A1 Jul. 14, 2005

(30) Foreign Application Priority Data

Apr. 30, 2002 (DE) .................. 102 19 375

(51) Int. Cl.
*C07C 7/08* (2006.01)
(52) U.S. Cl. .............. 585/864; 208/313; 208/320; 208/326; 208/330; 585/833; 585/860
(58) Field of Classification Search ........... 585/864, 585/860, 833; 208/317, 313, 320
See application file for complete search history.

(56) References Cited

U.S. PATENT DOCUMENTS

| 4,162,198 A | * | 7/1979 | Stockburger et al. | 203/23 |
| 4,515,661 A | * | 5/1985 | Ogura et al. | 203/60 |
| 4,555,312 A | | 11/1985 | Ogura et al. | |
| 6,337,429 B1 | * | 1/2002 | Kindler et al. | 585/864 |
| 2006/0241329 A1 | * | 10/2006 | Heida | 585/809 |

FOREIGN PATENT DOCUMENTS

| DE | 27 24 365 | 11/1978 |
| DE | 198 18 810 | 10/1999 |
| EP | 079 679 | 10/1981 |

* cited by examiner

*Primary Examiner*—Tam M. Nguyen
(74) *Attorney, Agent, or Firm*—Oblon, Spivak, McClelland, Maier & Neustadt, P.C.

(57) ABSTRACT

A continuous process for isolating butenes from a C₄ fraction comprising butanes, butenes and other $C_3$-$C_5$-hydrocarbons by extractive distillation using a selective solvent (LM), comprising a first process stage I in a scrubbing zone (E) and a second process stage II in a degassing zone (A), wherein the liquid or a substream of the liquid is taken off from the degassing zone (A) at a theoretical plate located one or more theoretical plates below the feed point for the bottom stream (LM/$C_4H_8$) from the scrubbing zone (E), heated and/or vaporized by indirect heat exchange with the hot bottom stream (LM) from the degassing zone (A) and returned to the degassing zone (A) at the same theoretical plate or above this, with the theoretical plate from which the liquid or substream of liquid is taken off being selected so that the total energy requirement in the process stages I and II is minimized, is proposed.

14 Claims, 2 Drawing Sheets

CONTINUOUS METHOD FOR OBTAINING BUTENES FROM A $C_4$ FRACTION

Figure 1:
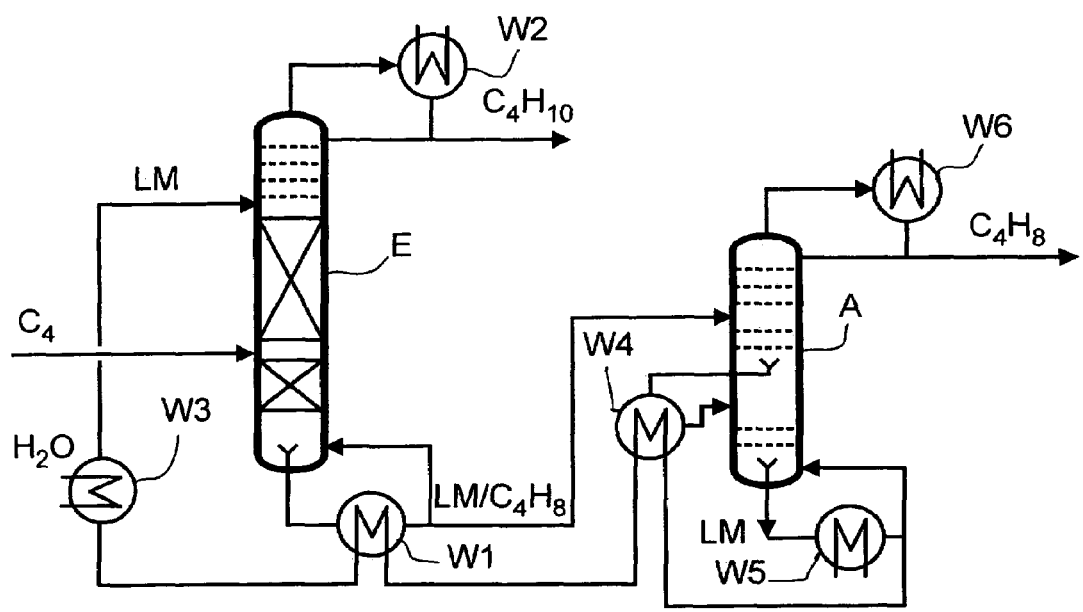

The present invention relates to a continuous process for isolating butenes from a $C_4$ fraction by extractive distillation using a selective solvent.

The term $C_4$ fraction refers to mixtures of hydrocarbons having predominantly 4 carbon atoms per molecule. $C_4$ fractions are obtained, for example, in the production of ethylene and/or propylene by thermal cracking of a petroleum fraction such as liquefied petroleum gas, naphthyl or gas oil. $C_4$ fractions are also obtained in the catalytic dehydrogenation of n-butane and/or n-butene. $C_4$ fractions generally comprise butanes, n-butene, isobutene, 1,3-butadiene, together with small amounts of other hydrocarbons, and also butynes, in particular 1-butyne(ethylacetylene) and butenyne(vinylacetylene). The 1,3-butadiene content is generally from 10 to 80% by weight, preferably from 20 to 70% by weight, in particular from 30 to 60% by weight, while the content of vinylacetylene and ethylacetylene generally does not exceed 5% by weight.

The fractionation of $C_4$ fractions is a complicated distillation problem because of the small differences in the relative volatilities of the components. Fractionation is therefore carried out by extractive distillation, i.e. a distillation with addition of a selective solvent (also referred to as extractant) which has a boiling point higher than that of the mixture to be fractionated and increases the differences in the relative volatilities of the components to be separated.

Many processes are known for the fractionation of $C_4$ fractions by means of extractive distillation using selective solvents. In all of them, the gaseous $C_4$ fraction to be fractionated is brought into countercurrent contact with the liquid selective solvent under appropriate thermodynamic conditions, generally at low temperatures, frequently at room temperature or at slightly elevated temperature, and at atmospheric pressure, so that the selective solvent is loaded with the components of the $C_4$ fraction for which it has a relatively high affinity, i.e. unsaturated or multiply unsaturated components, while the saturated components remain in the vapor phase and are taken off at the top. The unsaturated or multiply unsaturated components are subsequently fractionally liberated from the laden solvent stream, i.e. released as gas from the selective solvent, in one or more further process steps under suitable thermodynamic conditions, i.e. at higher temperature and/or lower pressure, compared to the first process step. The degassed solvent is, after being cooled, generally in an integrated heat system in which the heat is utilized for increasing the temperature of the feed stream to be fed to degassing, recycled to the first process step, i.e. to the extractive distillation of the $C_4$ fraction. Such processes are known, for example, from DE-A 198 188 10 or DE-A 27 24 365.

It is an object of the present invention to provide a process for isolating butenes from a $C_4$ fraction by extractive distillation using a selective solvent, which process is particularly efficient and economical. In particular, the amounts of energy required and the capital costs should be low in this process.

The achievement of this object starts out from a continuous process for isolating butenes from a $C_4$ fraction comprising butanes, butenes and possibly traces of other hydrocarbons by extractive distillation using a selective solvent, in which the $C_4$ fraction is, in a first process stage I, separated in a scrubbing zone into which the $C_4$ fraction is fed in gaseous or liquid form and the selective solvent is fed in liquid form above the feed point of the $C_4$ fraction into a butane-containing top stream and a bottom stream comprising the selective solvent laden with the butenes and possibly traces of other hydrocarbons, and the bottom stream is, in a second process stage II, separated in a degassing zone to which energy is fed via a bottom vaporizer and which is at a higher temperature and/or lower pressure than the scrubbing zone into a top stream comprising the butenes and any traces of other hydrocarbons and a bottom stream comprising the selective solvent, with the heat of the bottom stream from the degassing zone being utilized for increasing the temperature in the degassing zone.

In the process of the present invention, the liquid or a substream of the liquid is taken off from the degassing zone at a theoretical plate located one or more theoretical plates below the feed point for the bottom stream from the scrubbing zone, heated and/or vaporized by indirect heat exchange with the hot bottom stream from the degassing zone and returned to the degassing zone at the same theoretical plate or above this, with the theoretical plate from which the liquid or substream of liquid is taken off being selected so that the total energy requirement in the process stages I and II is minimized.

The present process can in principle be applied to any $C_4$ fraction, but it is particularly advantageous to use $C_4$ fractions which have a relatively high proportion of butenes as starting mixture.

For the purposes of the present invention, traces of other hydrocarbons are proportions by weight of other hydrocarbons which do not adversely affect the specifications of the products obtained from the $C_4$ fraction in subsequent use.

Starting materials which can advantageously be used are, for example, $C_4$ fractions from an oil refinery, from FCC (Fluidized Catalytic Cracking) plants, which generally have a composition of from 20 to 70% by weight of butanes, from 30 to 80% by weight of butenes together with other $C_3$-$C_5$-hydrocarbons as balance, particularly preferably $C_4$ fractions comprising 42% by weight of butanes, 56% by weight of butenes and 2% by weight of other $C_3$-$C_5$-hydrocarbons.

A typical $C_4$ fraction from an FCC plant has the following composition, in % by weight:

| | |
|---|---|
| propane | 0.3 |
| propene | 1.2 |
| n-butane | 12 |
| i-butane | 30 |
| 1-butene | 14 |
| i-butene | 10 |
| trans-2-butene | 15.5 |
| cis-2-butene | 16.5 |
| 1,3-butadiene | 0.5. |

Another $C_4$ fraction which can advantageously be used in the present process is raffinate 1 from a butadiene plant. This is preferably used directly without further intermediate treatment.

In butadiene plants, 1,3-butadiene is isolated from $C_4$ fractions in which it is present, with the $C_4$ fractions used typically having compositions in % by weight in the following ranges:

| | |
|---|---|
| 1,3-butadiene | from 10 to 80 |
| butenes | from 10 to 60 |
| butanes | from 5 to 40 |
| other $C_4$-hydrocarbons and other hydrocarbons, in particular $C_3$- and $C_5$-hydrocarbons | from 0.1 to 5 |
| | from 0 to a maximum 5. |

In butadiene plants, the $C_4$ fraction to be fractionated is firstly brought in gaseous form into countercurrent contact with the liquid selective solvent in an extraction zone in which the 1,3-butadiene and further hydrocarbons for which the selective solvent has a higher affinity than for 1,3-butadiene are essentially completely absorbed by the selective solvent but the components for which the selective solvent has a lower affinity, in particular the butanes and the butenes, mostly remain in the gas phase. This gas phase is taken off as top stream and is frequently referred to as raffinate 1. In the process of DE 198 188 10, the raffinate 1 is the top stream designated as Gbc from the extractive distillation column EI in FIGS. 1 and 2.

In the process of DE-A 27 24 365, the raffinate 1 is the top stream from the main scrubber.

An illustrative composition for raffinate 1 in % by weight is shown below:

| | |
|---|---|
| n-butane | 17 |
| i-butane | 6 |
| 1-butene | 29 |
| i-butene | 36 |
| trans-2-butene | 6 |
| cis-2-butene | 6 |
| 1,3-butadiene | $\leq 0.01$ |

The present separation task can be carried out using selective solvents whose affinity for hydrocarbons increases with the presence of double bonds and further with the presence of conjugated double bonds and triple bonds, preferably dipolar, particularly preferably dipolar aprotic, solvents. To simplify the choice of materials of construction for the apparatus, preference is given to substances which are noncorrosive or have a low corrosivity.

Selective solvents which are suitable for the process of the present invention are, for example, butyrolactone, nitriles such as acetonitrile, propionitrile, methoxypropionitrile, ketones such as acetone, furfural, N-alkyl-substituted lower aliphatic acid amides such as dimethylformamide, diethylformamide, dimethylacetamide, diethylacetamide, N-formylmorpholine, N-alkyl-substituted cyclic acid amides (lactams) such as N-alkylpyrrolidones, in particular N-methylpyrrolidone. In general, use is made of alkyl-substituted lower aliphatic acid amides or N-alkyl-substituted cyclic acid amides. Dimethylformamide, acetonitrile, furfural and especially N-methylpyrrolidone are particularly advantageous.

It is also possible to use mixtures of these solvents with one another, for example N-methylpyrrolidone with acetonitrile, mixtures of these solvents with cosolvents such as water and/or tert-butyl ethers, for example methyl tert-butyl ether, ethyl tert-butyl ether, propyl tert-butyl ether, n-butyl or isobutyl tert-butyl ether.

A particularly useful selective solvent is N-methylpyrrolidone, in the present text referred to as NMP for short, preferably in aqueous solution, advantageously with from 0 to 20% by weight of water, in particular from 7 to 10% by weight of water, particularly preferably 8.3% by weight of water.

Process Stage I

In process stage I, a $C_4$ fraction is subjected to extractive distillation in a scrubbing zone by feeding the $C_4$ fraction in gaseous or liquid, preferably in gaseous form and the selective solvent in liquid form above the feed point of the $C_4$ fraction into the scrubbing zone. In this countercurrent contact of $C_4$ fraction and solvent, the $C_4$ fraction is separated into a top stream comprising the saturated components, i.e. the components for which the selective solvent has a lower affinity, predominantly butanes, and a bottom stream which comprises the solvent laden with components for which the selective solvent has a higher affinity than for the butanes, predominantly butenes and any further hydrocarbons. Preferably the $C_4$ fraction is fed in gaseous form into scrubbing zone, in its lower region.

The scrubbing zone is generally configured as a column. There are in principle no restrictions regarding the separation-active internals which can be used in this: it is equally possible to use trays, random packing or structured packing. The column advantageously has from 10 to 80, preferably from 20 to 30, theoretical plates, in particular 26 theoretical plates.

Above the feed point for the selective solvent in the upper region of the column, there is preferably a backscrubbing zone comprising from 3 to 5 trays, in which residual selective solvent is scrubbed out by means of the runback condensed at the top of the column.

The column pressure in the scrubbing zone is dependent on the temperature of the cooling medium in the condenser at the top of the column (well water, river water, seawater, refrigerant such as liquid propylene, liquid ammonia or brine). It is generally from 1 to 15 bar, frequently from 2 to 10 bar, preferably 5.4 bar. The temperature in the column is, on the basis of the abovementioned pressure values, set so as to give suitable thermodynamic conditions under which the selective solvent becomes laden with the components of the $C_4$ fraction for which it has a greater affinity than for the butanes while the butanes in the $C_4$ fraction remain in the gas phase. The temperature at the top of the column is typically in the range from about 30 to 60° C.

Process Stage II

The bottom stream from the scrubbing zone is, in process stage II, separated in a degassing zone at a higher temperature and if appropriate lower pressure compared to the scrubbing zone into a top stream comprising the butenes and any traces of other hydrocarbons and a bottom stream comprising the selective solvent. Here, the heat of the bottom stream from the degassing zone is utilized by means of indirect heat exchange to increase the temperature of a liquid stream taken off from the degassing zone.

In the degassing zone, the thermodynamic conditions have to be set so that degassing of the hydrocarbons, in particular the butenes and any further $C_3$-$C_5$-hydrocarbons, from the selective solvent occurs. In general, if NMP containing from about 7 to 10% by weight of water is used as selective solvent, temperatures at the bottom in the range from 150 to 160° C. and pressures in the range from atmospheric pressure to 10 bar absolute, preferably 1.5 bar absolute, are necessary for this.

As regards the configuration in terms of apparatus, the degassing zone can, like the scrubbing zone, be a column which can in principle be equipped with any type of separation-active internals. Preference is given to using separation-active internals which have a low susceptibility to fouling or are easy to clean, in particular trays.

The column preferably has from 1 to 30 theoretical plates, in particular from 2 to 8 theoretical plates, particularly preferably four theoretical plates.

As in the case of the scrubbing zone, the degassing zone is preferably provided in the region above the inlet for the feed stream with backscrubbing trays for selective solvent entrained in the vapor stream, in general from 3 to 5 trays.

At the bottom of the degassing zone A, hot selective solvent is taken off as bottom stream. This is cooled in an integrated heat system, i.e. by utilizing its heat content within the process, and recycled to process stage I, i.e. to the scrubbing zone.

According to the present invention, the heat of the hot bottom stream from the degassing zone A is utilized particularly efficiently by means of a particular way of carrying out the process so that the total energy requirement for the process is minimized.

For this purpose, the liquid or a substream of the liquid is taken off from the degassing zone A at a theoretical plate located one or more theoretical plates below the feed point for the feed stream to the degassing zone, heated and/or vaporized by indirect heat exchange with the hot bottom stream from the degassing zone and returned to the degassing zone at the same theoretical plate from which the stream had been taken off.

Preferably the heat of the bottom stream from the degassing zone is used in addition in a washing zone, by taking off the liquid or a substream of the liquid from a theoretical plate in the washing zone, situated one or more theoretical plates below the feed point of the stream of the selective solvent, preferably below the feed point of the $C_4$ fraction, heating and/or vaporizing it with the hot bottom stream from the degassing zone and returning it to the same theoretical plate or above it into the washing zone, with the theoretical plate from which the stream or substream is taken off being selected so that the total energy requirement in the process stages I and II is minimized.

In a preferred process variant, the liquid stream or substream taken off is subjected to expansion evaporation to give a gaseous phase and a liquid phase and the gaseous and liquid phases are subsequently returned to the same theoretical plate from which the liquid stream or substream had been taken off or the gaseous part of the liquid stream or substream which was taken off is returned to a theoretical plate situated one or more theoretical plates above the theoretical plate from which the liquid stream or substream had been taken off.

The inventors have recognized that for each degassing zone there is, as a function of the feed composition, the temperature and pressure conditions, the number of theoretical plates and the prescribed specification for the desired product taken off as top stream, a particular theoretical plate at which indirect heat exchange with the hot bottom stream from the degassing zone is most advantageous, because here the least amount of energy has to be supplied from the outside to the bottom vaporizer of the degassing zone, i.e. the total energy requirement in the process stages I and II is minimized. If the liquid is taken off from a theoretical plate lower down, the temperature difference between this and the bottom stream is low as a result of the temperature profile in the degassing zone and little heat can therefore be transferred. On the other hand, if the liquid is taken off at a theoretical plate higher up, the following considerations apply: the largest quantity of heat can be transferred between the feed stream to the degassing zone and the hot bottom stream because the temperature difference is greatest. However, this is likewise not the most economical utilization of the energy of the bottom stream, since it results in introduction of more energy than is necessary for the separation task at this point. This excess energy has to be removed either by means of an unnecessarily high reflux ratio at the condenser at the top of the degassing zone or via an additional cooler.

If the hot solvent has not yet been cooled sufficiently by indirect heat exchange with the liquid taken off from the degassing zone to be able to be recycled to the extraction zone, the heat content which is still available can be utilized at another point in the process, preferably in the bottom vaporizer of the extraction zone of process stage I.

In a preferred process variant, the scrubbing zone and degassing zone are located in a single column. As a result, the capital costs and operating costs are significantly lower and the plant is safer to operate.

The invention is illustrated below with the aid of a drawing and examples.

Figure 2:
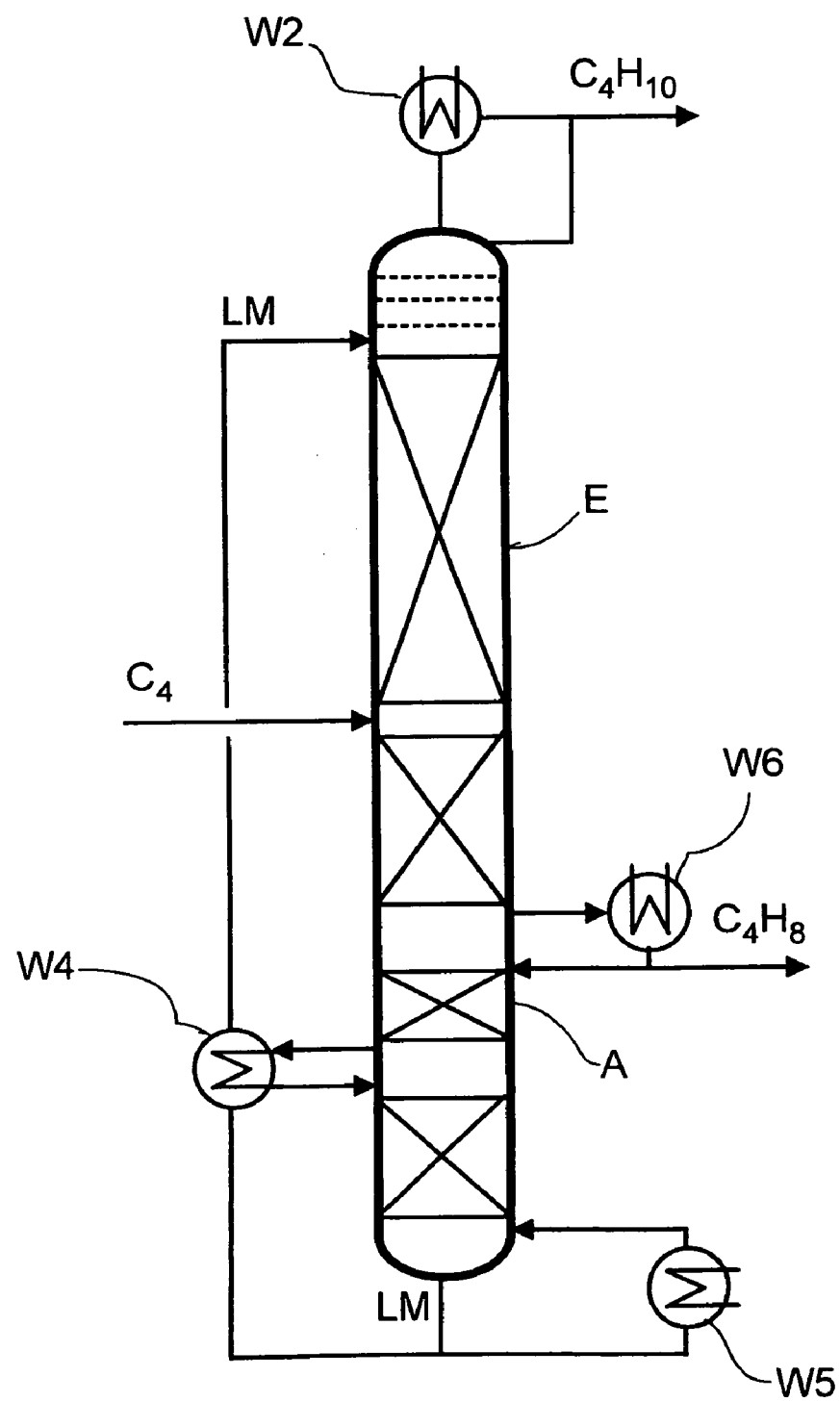

In the figures:

FIG. 1 schematically shows a preferred plant for carrying out the process of the present invention, FIG. 2 schematically shows a further preferred plant in which the scrubbing zone and the degassing zone are both located in a single column.

In the figures, identical reference numerals refer to identical or corresponding features.

FIG. 1 shows a scrubbing zone E for extractive distillation which is configured as a column, with an inlet for the liquid solvent LM in the upper region of the column and an inlet for the gaseous $C_4$ fraction, stream $C_4$, in the lower region of the column. A top stream, $C_4H_{10}$, comprising predominantly the butanes is take off from the top of the column and a bottom stream, stream $LM/C_4H_8$, comprising solvent laden with, in particular, butenes and traces of other hydrocarbons is taken off at the bottom. The top stream is condensed in a condenser W2 at the top of the column. Part of this is preferably returned as runback to the top of the column. A heat exchanger W1 is located at the bottom of the column. To set the temperature of the selective solvent LM appropriately, a heat exchanger W3, which is preferably operated by means of water, can be provided. The bottom stream $LM/C_4H_8$ from the scrubbing zone E is introduced into a degassing zone A in its upper region. Energy is supplied from the outside to the degassing zone A via the bottom vaporizer W5. The top stream from the degassing zone A is condensed in the condenser W6 at the top of the column, and part of it is returned as runback to the top of the column and the remainder is taken off as desired product, stream $C_4H_8$, comprising predominantly butenes. The hot bottom stream LM from the degassing zone A, which comprises predominantly the solvent, transfers part of its heat content by indirect heat exchange in the heat exchanger W4 to the liquid which is taken off from the degassing zone A at a theoretical plate located below the inlet for the feed stream and is returned to the degassing zone A after heating.

FIG. 2 schematically shows a plant in which the scrubbing zone E and the degassing zone A are both located in a single column.

Liquid solvent LM is fed into the upper region of the upper section of a column, which is configured as a scrubbing zone E, and gaseous $C_4$ fraction, stream $C_4$, is fed into the lower region of this section. A top stream, $C_4H_{10}$, comprising predominantly the butanes is taken off from the column, condensed in a condenser W2 at the top of the column and part of the condensate is returned as runback to the top of the column. The liquid from the lower region of the scrubbing zone E flows down into the lower section of the column, which represents the degassing zone A.

Energy is supplied from the outside to the degassing zone A via the bottom vaporizer W5. A stream is taken off from the upper region of the degassing zone, condensed in a condenser W6 and part of the condensate is returned as runback to the degassing zone A and the remainder is taken off as desired product, stream $C_4H_8$, comprising predominantly butenes. The hot bottom stream LM from the degassing zone A, which comprises predominantly the solvent, transfers part of its heat content by indirect heat exchange in the heat exchanger W4 to the liquid which is taken off from the degassing zone A and, after heating, returned to the degassing zone A.

Customary trays, ordered packing, random packing or the like can be used as separation-active internals.

The invention is illustrated further below with the aid of an example:

In a plant as shown schematically in FIG. 1, having 30 theoretical plates in a scrubbing zone E, a gaseous $C_4$ fraction, stream $C_4$, having the composition shown below was fed at a flow rate of 13 666 kg/h to the 9$^{th}$ theoretical plate counted from the bottom upward in the column, and a liquid solvent stream LM having the composition shown below, in each case in % by weight, was fed to the 27$^{th}$ theoretical plate.

Composition of the stream $C_4$:

| | |
|---|---|
| n-butane | 17.1 |
| i-butane | 6.4 |
| n-butene | 27.8 |
| i-butene | 33.8 |
| trans-2-butene | 8.6 |
| cis-2-butene | 6.23 |
| 1,3-butadiene | 0.07 |

Composition of the stream LM:

| | |
|---|---|
| NMP | 91.7 |
| Water | 8.3 |

Three theoretical backscrubbing plates were located in the column above the feed point for the solvent stream LM. The temperature of the stream $C_4$ was 41.7° C., the temperature of the stream LM was 34° C. and the pressure at the top of the column was 4.05 bar.

The top stream from the scrubbing zone E was condensed in a heat exchanger W2 and part of the condensate was returned as runback to the top of the column and the remainder was taken off as stream $C_4H_{10}$. The stream $C_4H_{10}$ comprised 95% of butanes, i.e. 25.6% by weight of n-butane, 69.4% by weight of i-butane, balance impurities, predominantly n-butene, trans-2-butene and water.

The bottom stream from the scrubbing zone E, LM/$C_4H_8$, comprised solvent laden with, in particular, butenes and traces of other hydrocarbons and had, by way of example, the following composition in % by weight:

| | |
|---|---|
| n-butane | 0.15 |
| i-butane | 0.30 |
| n-butene | 1.7 |
| i-butene | 2.1 |
| trans-2-butene | 0.53 |
| cis-2-butene | 0.39 |
| water | 7.8 |
| NMP | 87.3 |

The stream LM/$C_4H_8$ was introduced as feed stream at a temperature of 55.4° C. into a degassing zone A at the fourth, i.e. uppermost, theoretical plate. The top stream from the degassing zone A was condensed in a condenser W6 and the condensate was partly returned as runback to the degassing zone A and the remainder was taken off as stream $C_4H_8$ comprising predominantly butenes and having the composition shown below.

Composition of the stream $C_4H_8$ in % by weight:

| | |
|---|---|
| n-butene | 32.5 |
| i-butene | 40.0 |
| trans-2-butene | 10.1 |
| cis-2-butene | 7.3 |
| Balance: impurities. | |

Energy was supplied from the outside to the degassing zone A via the bottom vaporizer W5. The hot bottom stream LM from the degassing zone A, which comprised predominantly the solvent, transferred part of its heat content by indirect heat exchange in the heat exchanger W4 to the liquid which was in each case taken off from the degassing zone A at different theoretical plates and, after heating, returned to the degassing zone A. For example, liquid streams were in each case taken from the first, second, third or fourth theoretical plate of the degassing zone A and heated by heat integration, i.e. by indirect heat exchange with the hot solvent stream LM taken off from the bottom of the degassing zone A, and returned to the same theoretical plate.

The energy which had to be supplied from the outside to the bottom vaporizer W5 of the degassing zone A was as follows:

| Location of heat integration (theoretical plate) | Energy requirement in megawatt |
|---|---|
| 1 | 10.7 |
| 2 | 7.0 |
| 3 | 6.2 |
| 4 | 6.4 |
| Feed stream | 6.9 |

The experiments showed that the heat requirement for the plant, i.e. the energy which has to be supplied from the outside, can be minimized if the heat integration is carried out at the appropriate theoretical plate, in the present case the third theoretical plate which is one plate below the inlet for the feed stream. Heat integration into the feed stream is likewise unfavorable.

We claim:

1. A continuous process for isolating butenes from a $C_4$ fraction which comprises butanes, butenes and optionally traces of other hydrocarbons by extractive distillation using a selective solvent; the process comprising:

feeding the $C_4$ fraction in gaseous or liquid form into a scrubbing zone, feeding the selective solvent in liquid form into the scrubbing zone above the feed point of the $C_4$ fraction, separating the $C_4$ fraction into a first top stream comprising butane and a first bottom stream comprising the selective solvent laden with the butenes and optionally traces of other hydrocarbons, separating the first bottom stream into a second top stream comprising the butenes and said optional traces of other hydrocarbons and a second bottom stream comprising the selective solvent in a degassing zone, wherein energy is fed into the degassing zone via a bottom vaporizer, the temperature of the degassing zone is at a higher temperature and/or a lower pressure than the scrubbing zone, the heat of the second bottom stream from the degassing zone is utilized for increasing the temperature in the degassing zone, a first liquid or a substream of the first liquid is taken off from the degassing zone at a theoretical plate located one or more theoretical plates below the feed point for the first bottom stream from the scrubbing zone, heated and/or vaporized by indirect heat exchange with the second bottom stream from the degassing zone and returned to the degassing zone at or above the theoretical plate, wherein the theoretical plate from which the liquid or substream of liquid is taken off is selected to minimize the total energy requirement in the process.

2. The process as claimed in claim 1, wherein the $C_4$ fraction ($C_4$) is in gaseous form, and is fed into the scrubbing zone in the lower part thereof.

3. The process as claimed in claim 1, wherein a second liquid or a substream of the second liquid is taken off from the scrubbing zone from a theoretical plate located one or more theoretical plates below the feed point for the stream of selective solvent and below the feed point for the $C_4$ fraction, heated and/or vaporized by indirect heat exchange with the second bottom stream from the degassing zone and returned to the scrubbing zone at or above the theoretical plate, wherein the theoretical plate from which the liquid or substream of liquid is taken is selected to minimize the total energy requirement in the process.

4. The process as claimed in claim 1, wherein the selective solvent is selected from the group consisting of N-methylpyrrolidone, dimethylformamide, acetonitrile, furfural, mixture of N-methylpyrrolidone and at least one cosolvent, mixture of dimethylformamide and at least one cosolvent, mixture of acetonitrile and at least one cosolvent, mixture of furfural and at least one cosolvent, and mixtures thereof.

5. The process as claimed in claim 4, wherein the selective solvent comprises N-methylpyrrolidone and the N-methylpyrrolidone comprises from 0 to 20% by weight of water.

6. The process as claimed in claim 1, wherein the first liquid or the substream of the first liquid from the degassing zone is returned to the same theoretical plate from which the liquid or the substream of the liquid was taken off.

7. The process as claimed in claim 1, wherein the liquid stream or substream taken off is subjected to expansion evaporation to give a gaseous phase and a liquid phase and the gaseous and liquid phases are subsequently returned to the same theoretical plate from which the liquid stream or substream was taken off or the gaseous part of the liquid stream or substream which was taken off is returned to a theoretical plate located one or more theoretical plates above the theoretical plate from which the liquid stream or substream was taken off.

8. The process as claimed in claim 1, wherein the number of theoretical plates in the scrubbing zone is from 10 to 80, and the number of theoretical plates in the degassing zone is from 1 to 30.

9. The process as claimed in claim 1, wherein the scrubbing zone and the degassing zone are both located in a single column.

10. The process as claimed in claim 5, wherein N-methylpyrrolidone comprises from 7 to 10% by weight of water.

11. The process as claimed in claim 5, wherein N-methylpyrrolidone comprises 8.3% by weight of water.

12. The process as claimed in claim 3, wherein the first liquid or the substream of the first liquid from the degassing zone and/or the second liquid or the substream of the second liquid from the scrubbing zone is returned to the same theoretical plate from which the liquid or the substream of the liquid was taken off.

13. The process as claimed in claim 8, wherein the number of theoretical plates in the scrubbing zone is from 20 to 30 and the number of theoretical plates in the degassing zone is from 2 to 8.

14. The process as claimed in claim 8, wherein the number of theoretical plates in the scrubbing zone is 26 and the number of theoretical plates in the degassing zone is 4.

* * * * *